US007056745B2

(12) United States Patent
Lorber et al.

(10) Patent No.: US 7,056,745 B2
(45) Date of Patent: Jun. 6, 2006

(54) DIAGNOSTIC METHOD AND APPARATUS

(75) Inventors: Avraham Lorber, Metar (IL); Zeev Karpas, Omer (IL)

(73) Assignee: Q-Scent Ltd. (IL)

( * ) Notice: Subject to any disclaimer, the term of this patent is extended or adjusted under 35 U.S.C. 154(b) by 520 days.

(21) Appl. No.: 09/813,523

(22) Filed: Mar. 21, 2001

(65) Prior Publication Data

US 2002/0102627 A1    Aug. 1, 2002

(30) Foreign Application Priority Data

Feb. 1, 2001   (IL)   ..................... 141233

(51) Int. Cl.
*G01N 33/00*    (2006.01)
(52) U.S. Cl. ..................... 436/111; 436/811
(58) Field of Classification Search ............... 436/111, 436/811; 600/300; 702/23
See application file for complete search history.

(56) References Cited

U.S. PATENT DOCUMENTS

| 4,001,213 | A |   | 1/1977 | Hershman et al. |
| 4,080,488 | A |   | 3/1978 | Chen et al. ............... 429/111 |
| 5,109,691 | A | * | 5/1992 | Corrigan et al. ........... 73/23.36 |
| 5,856,616 | A |   | 1/1999 | Maswadeh et al. |
| 6,387,329 | B1 |  | 5/2002 | Lewis et al. |
| 6,428,748 | B1 |  | 8/2002 | Wallach |

FOREIGN PATENT DOCUMENTS

WO      WO 00/20852 A1    4/2000

OTHER PUBLICATIONS

Suh, Ja Won, et al. "Urinary Polymine Evaluation For Effective Diagnonosis Of Various Cancers" J. Chromatog. B, vol. 688 (1997) pp. 179-186.
Chen, K.C.S., et al. "Biochemical Diagnosis Of Vaginitis: Determination Of Diamines In Vaginal Fluid" J. Infect. Dis. vol. 145 (1982), pp. 337-345.
Karpas, Z., "Ion Mobility Spectromerty Of Aliohatic And Aromatic Amines" Chem., vol. 61, (1989) ,pp. 684-689.
Baumbach, J.I., et al., Appl. Spectrosc, Ion Mobility Spectrometry: Arriving On Site And Moving Beyond A Low Profile, vol. 53, (1999), pp. 338A-355A.

(Continued)

*Primary Examiner*—Monique T. Cole
(74) *Attorney, Agent, or Firm*—Lerner, David, Littenberg, Krumholz & Mentlik, LLP

(57) ABSTRACT

Diagnostic method, based on the amounts of biogenic amines that are contained in a body fluid or other sample. A number of measured parameters related to the desired diagnostic information are derived from the amounts. For each diagnostic information desired, an input consisting of the identification of the diagnostic information is provided. The input is compared to the measured parameters and a diagnostic response is derived from the comparison. The measured parameters may be derived from the amounts of the biogenic amines according to a program stored in a memory.

7 Claims, 4 Drawing Sheets

OTHER PUBLICATIONS

Lawrence, P.J. et al., "Spectrophotometric quantitation of vaginal fluid trimethylamine and comparative performance of olfactory trimethylamine (KOH whiff test) detection and a new colorimetric chemical test," Clinical Chemistry, vol. 45, No. 6 Part 2, Jun. 1999, p. A162 XP001118327 51st Annual Meeting of the American Associaion of Clinical Chemistry; New Orleans, LA, USA; Jul. 25-29, 1999 IISN: 0009-9147 abstract.

Karpas et al., "The Structure of Protonated Diamines and Polyamines," Struct. Chem., vol. 5, (1994) pp. 135-140.

* cited by examiner

DIAGNOSTIC METHOD AND APPARATUS

FIELD OF THE INVENTION

The invention relates to a method for diagnosing certain pathological conditions, particularly vaginal disorders, and to an apparatus for automatically providing such diagnoses or relevant diagnostic information.

BACKGROUND OF THE INVENTION

It is known in the art that the presence of biogenic amines in human body fluids may reveal or suggest pathological conditions and dysfunctions. For example, elevated levels of certain biogenic amines in urine may indicate the presence or the likelihood of the presence of a cancer (there are many papers dealing with this—see, for instance, Suh, J W, Lee, S H, Chung, B C, Park, J, *Urinary Polyamine Evaluation for Effective Diagnosis of Various Cancers*, Journal of Chromatography B, 1997, Vol. 688, Iss 2, pp. 179–186). Several of the types of vaginal diseases may be expressed in elevated levels of biogenic amines in vaginal discharge and fluids (see, for instance, C. S. Chen, R. Amsel, D. A. Eschenbach and K. K. Holmes, *Biochemical diagnosis of vaginitis: determination of diamines in vaginal fluid*, J. Infectious Disease 145 (1982), pp. 337–345).

Body fluids may include e.g. urine, blood, serum, saliva, vaginal discharge and fluids, etc. Further, samples in which the presence of biogenic amines may be determined may not be fluids, but, e.g., skin and tissues, swipe samples, etc. Even direct sniffing of skin or breath exhaled by a subject may provide information in this respect. This should be understood whenever body fluids are mentioned in this application.

Chemical changes in the living system or degradation processes of cells after death are accompanied with formation of molecular byproducts. These processes include the breaking down of peptides and DNA strands to smaller components, and changes in the building blocks, amino acids, leading to the formation of amines. Not only amino compounds are produced, but other, smaller molecules, such as aldehydes and alcohols are also formed. One of the processes of particular interest is the breakdown of amino acids and the production of diamines and polyamines. For example, decarboxylation of histidine, ornithine, lysine, produces histamine, putrescine and cadaverine respectively.

Several analytical methods have been proposed for the analysis of biogenic amines. Most of these are laboratory methods that require expensive equipment, extensive sample preparation and the skills of a trained analytical chemist or technician. Among these are high performance liquid chromatography (HPLC), or gas chromatography after derivatization of the samples. Biosensors may also be used, as well as various spectrometric techniques. Solid state sensors have also been proposed, but generally lack specificity.

Ion Mobility Spectrometry (also, briefly, IMS) is a known analytical method and its application for the determination of aliphatic and aromatic amines has been suggested: see, for instance, Z. Karpas, *Ion Mobility Spectrometry of Aliphatic and Aromatic Amines*, Anal. Chem. 61 (1989), 684. An apparatus for carrying out this method—the Ion Mobility Spectrometer (IMS)—is used primarily for detection, identification and monitoring of trace amounts of gases and vapors. It is particularly suitable for detection of compounds that have high proton affinity and form stable positive ions, or for compounds that have a high electronegativity and readily form stable negative ions. IMS is fully discussed in J. I. Baumbach and G. A. Eiceman, Appl. Spectrosc. 1999, vol.53, pp.338A–355A. However, any device that may be used for determining or measuring the mobility of ions may be used for carrying out the invention, and therefore any reference to IMS in this description and claims should not be construed as a limitation, but should be construed any including instrument for determining or measuring the mobility of ions.

The knowledge of the prior art as to the importance of biogenic amines for the possible detection of pathological conditions and as to the analysis of biogenic amines, including the use of IMS, has failed so far to provide a simple and reliable method for the diagnosis of vaginal disorders, particularly, though not exclusively, bacterial vaginosis that affects a large number of women. The provision of such a diagnostic method would constitute a valuable contribution to the medical art. However, such a method is not available: the detection of biogenic amines in vaginal fluids is known to suggest the presence of a pathological condition, but it does not provide specific and reliable information and merely suggests to the specialized physician the desirability of carrying out whatever tests and examinations may finally lead to a diagnosis.

Further, the present knowledge does not provide the practicing physician with an apparatus for the quick diagnosis of bacterial vaginosis and other pathological conditions, by a simple and direct way and without the application of knowledge and technology that are typical of different branches of science and are not found together in any physician, no matter how competent and dedicated. It would be extremely valuable to provide an instrument and method whereby the average physician could obtain from bodily fluids, quickly and in a reliable way, a diagnostic indication of specific diseases and/or pathological conditions, even though such a diagnostic indication may not be final and conclusive and may require, whether positive or negative, verification and integration.

It is therefore a purpose of this invention to provide method for the diagnosis of vaginal disorders, particularly, though not exclusively, bacterial vaginosis.

It is another purpose to provide a method for carrying out such diagnosis automatically and in real time.

It is a further purpose to provide, automatically and in real time, information of fundamental value in the diagnosis of a variety of pathological conditions.

It is a still further purpose to provide an apparatus for the quick diagnosis of bacterial vaginosis and other pathological conditions.

It is a still further purpose to provide a portable instrument that is capable of carrying out the spectrometry of bodily fluids and automatically derive from said spectrometry significant diagnostic indications.

It is a still further purpose to provide such an instrument that can be directed to provide diagnostic indications for specific diseases and/or pathological conditions.

It is a still further purpose to provide such an instrument that consists of the combination of components known in the art and readily available.

It is a still further purpose to provide such an instrument that can be widely used by physicians and medical institutions and is not excessively expensive.

It is a still further purpose to provide such an instrument which can be used, with the due precautions and warnings, by persons other than physicians and even by the patients themselves.

It is a still further purpose to provide such an instrument which can be used for purposes that are not diagnostic purposes, but are relevant to the public health, for instance, the control of the condition of food, such as, but not exclusively, the freshness of meat, fish and their products, as well as and seafood.

It is a still further purpose to provide such an instrument that permits instant examination of tissues removed during an operation as an indication for malignant tissues.

SUMMARY OF THE INVENTION

The invention provides a method for the diagnosis of bacterial vaginosis which comprises determining the presence of trimethylamine (hereinafter, TMA) ions in vaginal fluid. According to the method, preferably, the total amount of amine ions is measured, and if the number of TMA ions is 40% or more the total number of amine ions, the presence of bacterial vaginosis is recognized, while if the number of TMA ions is 20% or less, the absence of bacterial vaginosis is recognized. The ratio of the number of ions of a given amine to the total number of amine ions could also be called "equivalent ratio" or "concentration of the given amine by equivalents".

Levels of putrescine and cadaverine are also measured, according to the invention, and if the number of their ions is above 10% of the total number of amine ions, various pathological conditions are suspected, as will be detailed hereinafter.

A way of carrying out the method of the invention is the following:

(1) the presence of volatile amine compounds, including tertiary amines like trimethylamine (TMA) and other amines, diamines like putrescine and cadaverine as well as polyamines like spermidine and spermine is measured by the appearance of ions derived from these substances in the ion mobility measurement.
(2) samples of the vaginal fluid, either on a sterile applicator or by any other method, are placed in sample holder or introduction system, and vapors emanating from said sample are ionized, forming ions that are specific for the said substances.
(3) enhancement of vapor emanation may be carried out by the addition of an appropriate chemical reagent, that transforms the complex amine compounds, like salts and acidic forms, to more volatile forms, which reagent, For example, can be comprised of an alkaline solution, like KOH, NaOH and/or ammonia.
(4) a direct device for sampling vapors emanating from the vaginal area may be used to transfer said vapors directly to a measuring device.
(5) control of the ion chemistry by addition of a reagent substance, comprising a volatile amine with proton affinity above that of most common interfering compounds but below that of said amine compounds, may be used to improve the ability to detect the presence of said amine substances.

The invention also provides a diagnostic apparatus which comprises:
a) an apparatus for measuring the mobility of ions, e.g. an Ion Mobility Spectrometer (IMS) for the determination of the amounts of biogenic amines contained in a body fluid or other sample;
b) a first elaborator means for deriving from said amounts a number of parameters related to the diagnostic information that is desired in any specific case;
c) buffer memory means for storing the parameters derived from the aforesaid determination of the amounts of biogenic amines—hereinafter, "the measured parameters";
d) a second elaborator means for deriving, from an input consisting of the identification of the diagnostic information desired and of the measured parameters, a diagnostic response.
e) memory means for storing programs controlling the operations of the first and second eleborator and for memorizing comparative parameters related to said diagnostic information.

The first and second elaborator means may consist of computer means and may be comprised together in a single computer. However, use may be made in certain cases of tables—LUTs—in place of computers or parts of computers.

The diagnostic response may be in some cases the statement of the presence of a disease or a pathological condition, or the statement that such a disease or pathological condition is suspected and its presence must be verified, or similar statements relative to the absence of a disease or pathological condition, or the statement that no conclusion can be drawn from the measured parameters or that no conclusion can be drawn for other reasons.

A similar response can be obtained from the apparatus if it is used not for diagnostic purposes, but for checking food.

The Ion Mobility Spectrometer will provide a spectrum of the biogenic amines, including peaks for certain amines. Ion mobility measurements by other methods would likewise provide a quantitative value for the presence of certain amines. The first elaborator will be so programmed that it will firstly select the amines that are relevant for the specific response that should be given. Based on said selection, the elaborator will decide whether the measured parameters should comprise the height of the peaks of the relevant amines or areas of the spectrum about said peaks, within certain predetermined ranges, or other parameters which will be defined by the first elaborator program. Similar parameters, of course, may be determined, if needed, for the amines that are not related to the specific response to be given. Alternatively, the measured parameters may be constituted by ratios between heights of peaks or areas of the spectrum. The measured parameters need not be memorized permanently, and therefore are stored in a buffer memory, but if required, may be transferred from the buffer memory to the permanent one.

The permanent memory of the apparatus will contain comparative parameters for each response possibly desired. Comparative parameters will be easily provided by determining the spectra of bodily fluids of different subjects that are free of the disease or pathological condition to which said response refers, determining the measured parameters of said subjects, and averaging said measured parameters of a sufficient number of subjects. Of course, the average may not be a simple mathematical average, but the measured parameters of each subject may be weighted by coefficients which take into account the specific characteristics of each subject, including any characteristics that are relevant to the specific response in question. For instance, if the presence of prostate cancer is to be determined, the age of the subjects tested will be an extremely relevant characteristic. Of course, in such a case, different comparative parameters may be memorized for different ages of subjects. The physicians that will program the first elaborator will know what characteristics are relevant and will know how to determine the comparative parameters for each disease or pathological condition.

The second elaborator will be programmed to determine from the differences between the measured parameters and the comparative parameters the likelihood of the presence of the disease or pathological condition being considered. The program will comprise determining the difference between said measured and said comparative parameters, defined in any suitable way, for instance, as a ratio of numerical values or as a value derived from a predetermined formula relating to the specific response desired; and deriving, from another predetermined formula or from the response to a number of typical questions, an index of the probability of the presence of the disease or pathological condition in question, or a response that is more complex than the mere indication of an index.

In its broader aspects, and beyond the specific aspect of diagnosing bacterial vaginitis and related pathological conditions, the method of the invention comprises the steps of:
a) determining the amounts of biogenic amines contained in a body fluid or other sample;
b) deriving from said amounts a number of measured parameters related to the desired diagnostic information;
c) providing, for each diagnostic information desired, an input consisting of the identification of said diagnostic information;
d) comparing said input to said measured parameters; and
e) deriving from said comparison a diagnostic response.

Step a) is carried out for each diagnostic operation and its results may be stored in a buffer memory. Step b) may be carried out according to a program stored in a buffer or permanent memory. Step c) may be carried out distinctly for each diagnostic operation, or may be have been carried out previously for a number of expected such operations and the results may be stored in a buffer or permanent memory. Step e) will be carried out according to a stored program that will associate a diagnostic response to results of the comparison of the aforesaid input to said measured parameter, for each of the expected diagnostic operations; but such a program may be derived, for particular cases, if it is not stored. It will be obvious that, if the invention is carried out for checking food, the diagnostic response will only consist in classifying food according to its edibility, e.g. as safe, doubtful, or spoiled.

DETAILED DESCRIPTION OF PREFERRED EMBODIMENTS

A first example of the invention will be given with reference to a diagnostic response relative to cancer.

In this example, the Ion Mobility Spectrometers (IMS) used were PhemtoChem-100 made by PCP Inc., West Palm Beach, Fla., USA and PTIMS made by Rotem Industries, Mishor Yamin, Israel. However, any properly equipped IMS made be used to obtain such spectra. The first and second elaborators, in this example, are combined into a single computer which comprises a permanent memory, a buffer memory, a CPU, a screen, a BUS providing the necessary electrical connections, power means, a keyboard, and all obvious accessories. Generally, IMS may display the biogenic amine spectrum or display their results in the form of a histogram series of bars or as a table of compounds. In any case, the IMS transmits to the buffer memory the amine spectrum. The operator has chosen, by means of the keyboard, the type of response which he wants. In this case, he has chosen a response which relates to the presence of a cancer. The CPU is programmed to draw from the buffer memory the data of the amine spectrum and calculate from them the measured parameters which are relevant to the diagnosis of cancer, according to a program which is stored in the permanent memory and which the CPU has drawn from said memory once the operator's choice has been made. The CPU also draws from the permanent memory the comparative parameters and carries out the necessary comparison to draw the response required.

Figure 1:
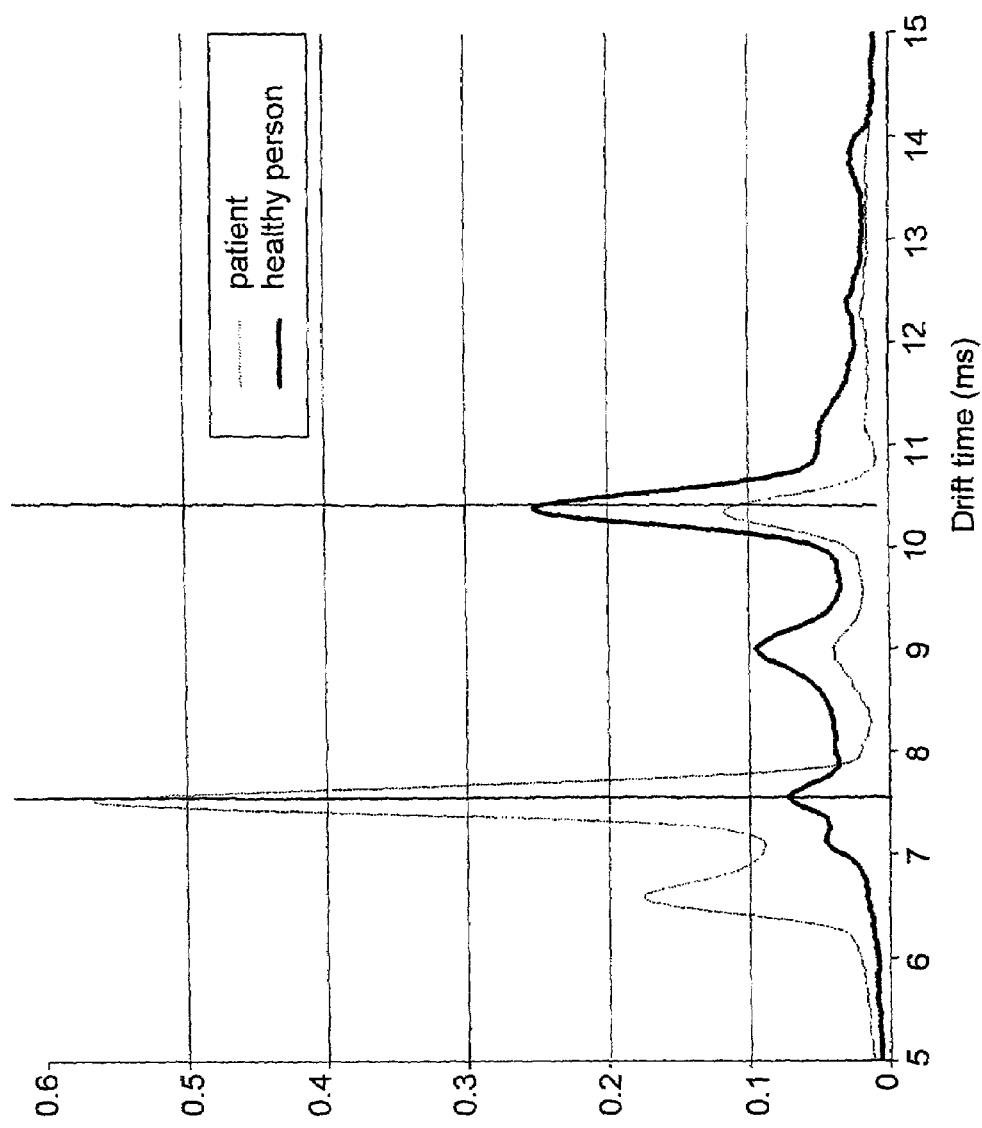
FIG. 1 shows the biogenic amine spectrum of the urine of a cancer patient and the comparable spectrum of a healthy subject.

FIG. 1 shows two curves relating to a healthy person and to a cancer patient respectively, as indicated in the drawing. The abscissa is the time at which the various amines appear and the ordinate is their amount, and since the various amines appear at different time, each curve constitutes an amine spectrum. The different peaks that appear permit to diagnose the presence of a disease, in this case cancer.

Figure 2:
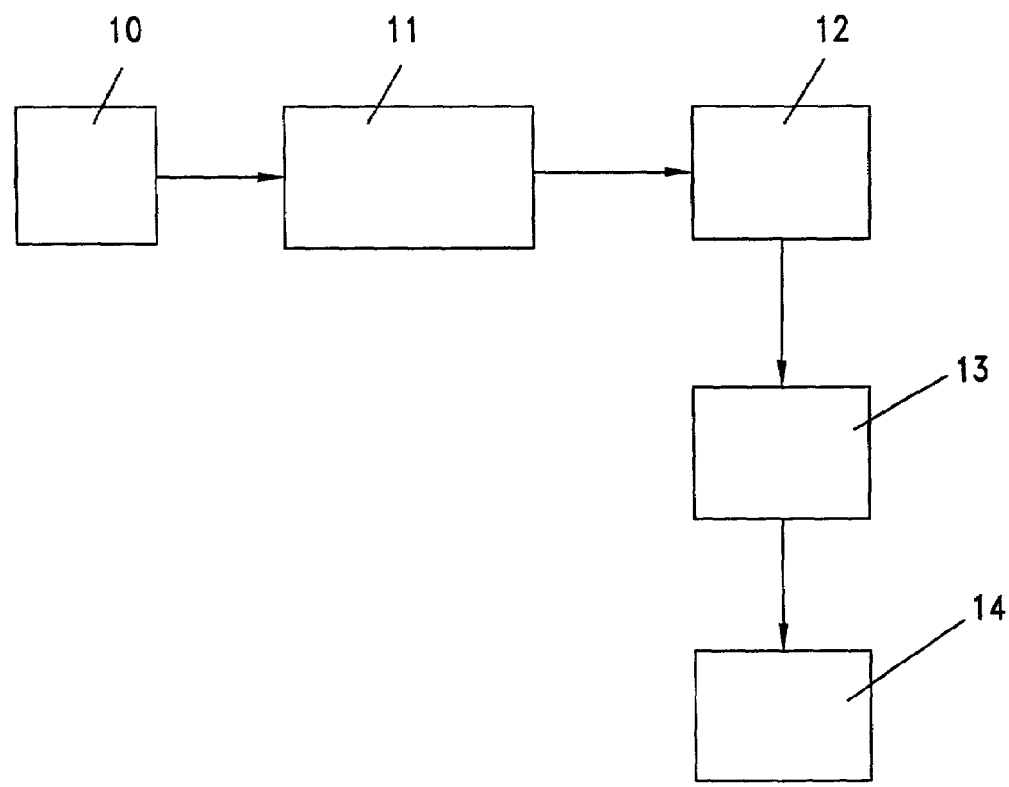
FIG. 2 is a schematic block diagram of the apparatus of the invention.

A block diagram of an apparatus for carrying out the invention is given in FIG. 2. In said figure, numeral 10 indicates a chemical reaction chamber. 11 is an ion mobility measurement device, e.g. an IMS. 12 is an analog-to-digital converter for the acquisition, from the ion mobility measurements, of the data that are considered relevant. 13 is a processor for processing the acquired data according to a predetermined program. 14 is an output device that shows the presence or absence or suspicion of presence of predetermined pathological conditions.

The following flowsheet of operations illustrates an embodiment of the invention:
a) Insert sample into chemical chamber
b) Add chemical reagent(s) to enhance emanation of volatile compounds
c) Transport vapors into ionization region of the IMS
d) Ionize vapors directly and through chemical gas-phase ion-molecule reactions
e) Detect ions, measure their mobility and quantify them.
f) Acquire data or spectra
g) Process data and compare to stored data (library, spectra or tables).
h) Output the result: Presence/absence of condition or Suspicion that the condition exists.

Figure 3:
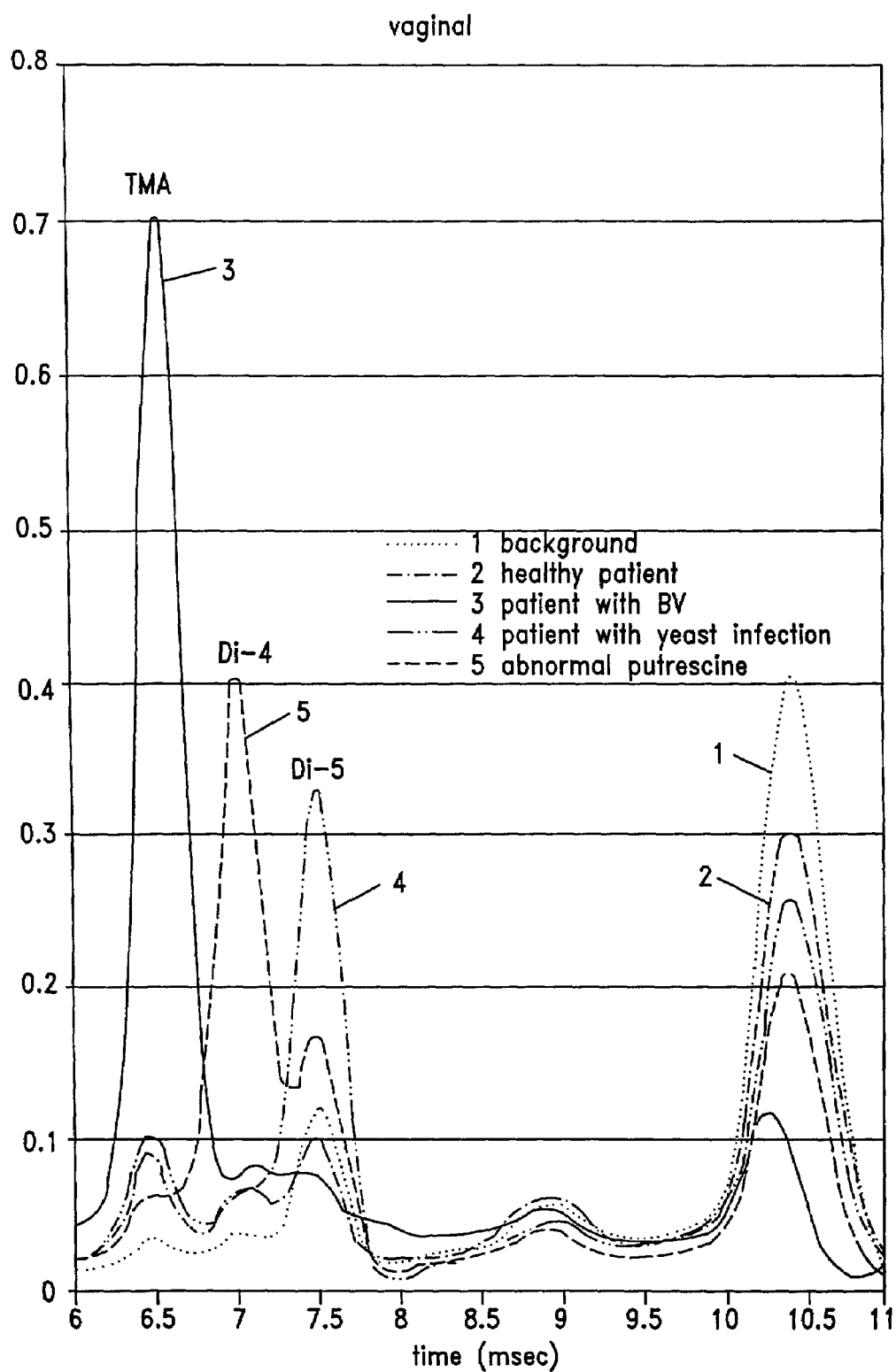
FIG. 3 is a diagram showing the peaks indicating the evolution of amines vapors from a number vaginal fluid samples.

FIG. 3 comprises a diagram, showing various curves, relative to different vaginal fluid samples. Vapors emanating from each sample were ionized, and the amounts of ions from different amines, particularly TMA, putrescine and cadaverine were measured. The vapors emanate at the same time, but the ions formed from the different compounds have different mobilities, so that when they are measured and reported as in FIG. 3 as a function of time, the peaks of the diagram indicate the amounts of the different amines that are recognized from the time at which they give a signal. The peaks relating to TMA, putrescine and cadaverine are indicated in FIG. 3 as TMA, Di-4 and Di-5 respectively. The curves relative to the various samples are identified by numbers at the side of FIG. 3 and it is seen that sample No.3 has an abnormally high content of TMA, indicating bacterial vaginosis. Curve 1 is the background spectrum, obtained when a clean Q-tip is inserted into the chemical reaction chamber and 300 µL of 8N KOH solution are added. Curve 2 is the mobility spectrum obtained from a vaginal fluid sample of a healthy woman with no vaginal disorder. Curve 3 was obtained from a vaginal fluid sample of a woman diagnosed as having a vaginal infection identified as bacterial vaginosis (BV) according to the Amsel test. Curve 4 was obtained from a vaginal fluid sample of a woman diagnosed as having a vaginal yeast infection. The abnormally high level of putrescine seen in Curve 5 is indicative of an unspecified vaginal disorder or infection.

Figure 4:
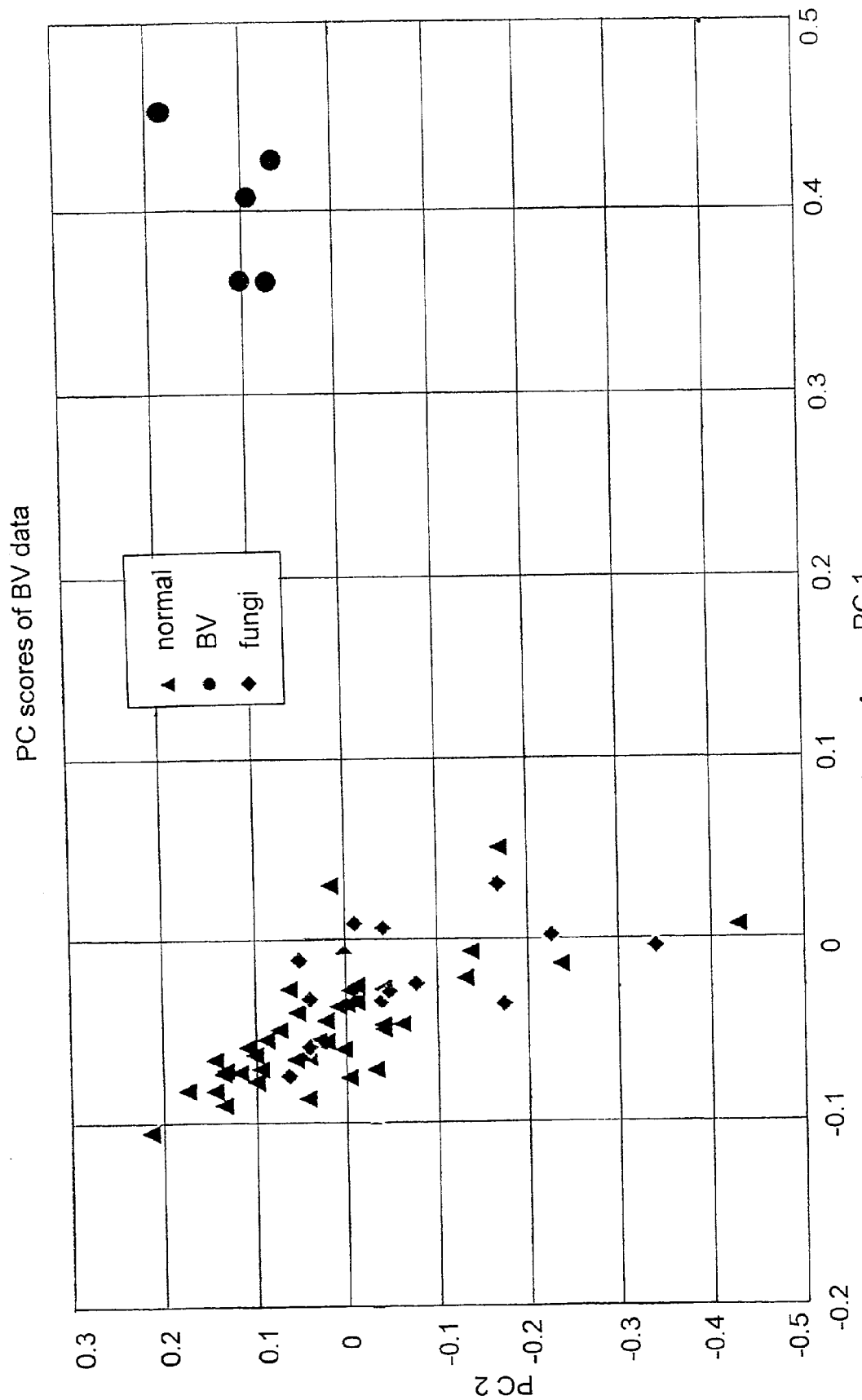
FIG. 4 is a diagram showing the Principal Component (PC) analysis of a number of vaginal fluid samples analyzed for Bacterial Vaginosis (BV).

FIG. 4 represents the scores of each mobility spectrum on the first two principal components (PC). The first principal component (the abscissa) represents the content of trimethylamine (TMA) in the mobility spectrum. The second principal component (the ordinate axis) represents the content of the diamines (putrescine and cadaverine). The cluster of points in the upper right hand corner (circles) is obtained from vaginal samples of women with bacterial vaginosis. The diamond shaped data points were obtained from vaginal samples diagnosed by the gynecologist as suffering from some vaginal disorder (yeast, trichomonas or elevated pH levels). The triangles represent vaginal samples taken from women with no reported or observed vaginal disorder.

The invention can also be applied, as set forth hereinbefore, for checking the freshness of meat.

While embodiments of the invention have been described by way of illustration, it will be apparent that the invention may be carried into practice with many modifications, variations and adaptations, without departing from the scope of the claims.

What is claimed is:

1. A method for diagnosing diseases or pathological conditions in a human patient comprising carrying out an ion mobility spectrometry measurement (IMS) on a bodily sample obtained from said patient, thereby determining an amount of ions formed by at least two biogenic amine contained in said sample further comprising calculating a ratio of the amounts of ions formed by said different biogenic amines in said sample, wherein said ratio is indicative of said disease or pathological condition.

2. The method of claim 1, wherein said bodily sample is a sample of vaginal fluid, wherein at least one of said amines comprises trimethylamine, and wherein said pathological conditions comprise vaginal disorders.

3. The method of claim 1, wherein said amines comprise putrescine and cadaverine.

4. The method of claim 1, comprising calculating the ratio of the amounts of ions formed by trimethylamine and ions formed by all biogenic amines present in said sample, and diagnosing the presence of bacterial vaginosis if said ratio is 0.4 or more.

5. The method of claim 1, comprising calculating the ratio of the amounts of ions formed by trimethylamine and ions formed by all biogenic amines present in said sample, and diagnosing the absence of bacterial vaginosis if said ratio is 0.2 or less.

6. The method of claim 3, wherein abnormally high amounts of putrescine or cadaverine indicate a pathological condition.

7. The method of claim 2, wherein said vaginal disorder is bacterial vaginosis.

* * * * *